United States Patent
Baracat-Nasr et al.

(10) Patent No.: US 9,844,498 B2
(45) Date of Patent: Dec. 19, 2017

(54) METHOD FOR MANUFACTURING A COSMETIC ARTICLE HAVING A DECORATIVE EMBOSSED AND/OR DEBOSSED SURFACE

(75) Inventors: Emeric Baracat-Nasr, Croissy-sur-Seine (FR); Xiaolu He, Shanghai (CN)

(73) Assignee: PARFUMS CHRISTIAN DIOR, Paris (FR)

( * ) Notice: Subject to any disclaimer, the term of this patent is extended or adjusted under 35 U.S.C. 154(b) by 270 days.

(21) Appl. No.: 14/408,860

(22) PCT Filed: Jul. 2, 2012

(86) PCT No.: PCT/CN2012/078049
§ 371 (c)(1),
(2), (4) Date: Oct. 16, 2015

(87) PCT Pub. No.: WO2014/005265
PCT Pub. Date: Jan. 19, 2014

(65) Prior Publication Data
US 2016/0030301 A1     Feb. 4, 2016

(51) Int. Cl.
*A61K 8/02*       (2006.01)
*A45D 40/00*  (2006.01)
*A45D 40/24*  (2006.01)

(52) U.S. Cl.
CPC ............ *A61K 8/0216* (2013.01); *A45D 40/00* (2013.01); *A45D 40/24* (2013.01); *A45D 2040/0012* (2013.01)

(58) Field of Classification Search
CPC ......................... A61K 8/0216; A61K 8/0237
(Continued)

(56) References Cited

U.S. PATENT DOCUMENTS 6,245,341 B1 * 6/2001 Pahlck ............... A45D 33/00
424/401
2005/0218560 A1 10/2005 Booth
(Continued)

FOREIGN PATENT DOCUMENTS

CN       1124860 A      6/1996
CN    201046595 Y      4/2008
(Continued)

OTHER PUBLICATIONS

Electronic translation of FR 2956833.*
(Continued)

*Primary Examiner* — Jill Heitbrink
(74) *Attorney, Agent, or Firm* — Miller, Matthias & Hull LLP

(57) ABSTRACT

The invention relates to a method of manufacturing a cosmetic article having a decorative embossed and/or debossed surface, based on at least one cosmetic product hot-poured into a container, this method making use of: a receptacle forming said container and having a peripheral wall and a bottom, said receptacle having at least one filling area, each filling area extending from the bottom of said receptacle and having a filling hole and at least one vent hole, and a closure member that cooperates with the receptacle to define an enclosed filling cavity with the at least one filling area, and having an embossed and/or debossed surface adapted to give the cosmetic product poured into said cavity an embossed and/or debossed surface, said method comprising at least the following steps: a) positioning the receptacle on the closure member so that the embossed and/or debossed surface extends into the filling area; b) hot-injecting the cosmetic product into the filling cavity by means of a filling head inserted in the filling hole; c) separating the receptacle from the closure member.

18 Claims, 3 Drawing Sheets

(58) Field of Classification Search
USPC .......................................................... 264/273
See application file for complete search history.

(56) References Cited

U.S. PATENT DOCUMENTS

2006/0001193 A1    1/2006  Booth
2008/0143018 A1    6/2008  Lazzarini

FOREIGN PATENT DOCUMENTS

| CN | 101804684 A | 8/2010 |
| CN | 102380931 A | 3/2012 |
| FR | 2956833 | 2/2010 |

OTHER PUBLICATIONS

International Search report and Written Opinion for related International Application PCT/CN2012/078049; report dated Jul. 2, 2012.

* cited by examiner

METHOD FOR MANUFACTURING A COSMETIC ARTICLE HAVING A DECORATIVE EMBOSSED AND/OR DEBOSSED SURFACE

CROSS-REFERENCE TO RELATED APPLICATION

This Application is a 35 USC §371 US National Stage filing of International Application No. PCT/CN2012/0780849 filed on Jul. 2, 2012.

FIELD OF THE DISCLOSURE

The invention relates to methods for manufacturing cosmetic articles based on one or more cosmetic products hot-poured into a container, particularly lipstick, gloss, eyeliner, make-up foundation, etc.

BACKGROUND OF THE-DISCLOSURE

The invention more particularly relates to a method for manufacturing a cosmetic article having a decorative embossed and/or debossed surface.

Document US2006001193 describes an example of such a method, making use of a lower mold having an embossed and/or debossed surface and an upper mold, in which a cosmetic product is first poured into the lower mold through a large opening formed in the upper mold, then the upper mold is removed and a container such as a cosmetic receptacle, possibly preheated, is applied to the molded cosmetic product. The receptacle holding the molded cosmetic product is then removed from the lower mold using a pressure fluid applied through passages formed in this lower mold.

The method described here uses a "picking" technique, which has the disadvantage that a space remains in the obtained article between the walls of the receptacle or jar and the molded cosmetic product. Under these conditions, the pattern on the surface of the molded cosmetic product cannot be formed all the way to the edge of the wall of the receptacle, which affects the aesthetics of the cosmetic article obtained.

The method described in document US2006001193 requires a preliminary step of molding the cosmetic product inside a mold, followed by a phase of transferring the molded cosmetic product into a final container formed by the receptacle, requiring a prior step of heating this receptacle, a step of accurately inserting the receptacle onto the cosmetic product, and a step of ejecting the assembly formed by the receptacle and the cosmetic product. This succession of steps results in a complex and costly method.

The aim of the invention is to eliminate these disadvantages.

SUMMARY OF THE DISCLOSURE

For this purpose, the invention proposes a method for manufacturing a cosmetic article having a decorative embossed and/or debossed surface, based on at least one cosmetic product hot-poured into a container, said method making use of:
a receptacle forming said container and having a peripheral wall and a bottom, said receptacle having at least one filling area, each filling area extending from the bottom of said receptacle and having a filling hole and at least one vent hole,
a closure member that cooperates with the receptacle to define an enclosed filling cavity with the at least one filling area, and having an embossed and/or debossed surface adapted to give the cosmetic product poured into said cavity an embossed and/or debossed surface, said method comprising at least the following steps:
a) positioning the receptacle on the closure member so that the embossed and/or debossed surface extends into the filling area;
b) hot injecting the cosmetic product into the filling cavity by means of a filling head inserted in the filling hole;
c) separating the receptacle from the closure member.

With these arrangements, it is simple, rapid, and inexpensive to create a cosmetic article formed of a receptacle and a cosmetic product poured directly into it, having a decorative embossed and/or debossed surface extending to the edges of the receptacle and in particular fully touching its peripheral wall. The pattern present on this decorative surface could represent a decorative and/or informative element, such as a decorative pattern, a logo, a brand, a personalized message, or information intrinsic to the poured cosmetic product, for example such as a SPF value (Sun Protection Factor).

In one advantageous arrangement, the method of the invention further makes use of a supporting frame having an opening for receiving the receptacle, said opening having a peripheral rim of a certain height (h), and the closure member having a support surface for the supporting frame, the embossed and/or debossed surface protruding beyond said support surface to a height that is at least equal to that of said rim. The method of the invention then further comprises a step consisting of placing the receptacle inside the opening of the supporting frame so that the peripheral wall of said receptacle rests on the rim, a step consisting of positioning the supporting frame on the closure member so that said rim rests on the support surface of said closure member, and a step consisting of separating the receptacle from the supporting frame.

In this manner, a decorative embossed and/or debossed surface can be formed on the obtained cosmetic article that is at most substantially flush with the edge of the peripheral wall of the receptacle on its open side.

Advantageously, step a) is preceded by the step of placing the receptacle inside the opening of the supporting frame, and step a) consists of positioning the supporting frame, equipped with the receptacle, on the closure member.

As a variant, step a) is preceded by the step of positioning the supporting frame on the closure member, and step a) consists of placing the receptacle inside the opening of the supporting frame positioned on the closure member.

In one arrangement of the invention, step c) consists of separating the receptacle from the closure member and from the supporting frame, with the latter remaining in place on said closure member.

As a variant, step c) consists of separating the supporting frame, equipped with the receptacle, from the closure member, and step c) is followed by the step consisting of separating the receptacle from the supporting frame.

Preferably, the supporting frame comprises at least one retaining element that cooperates with the bottom of the receptacle to prevent said receptacle from moving and possibly exiting through the opening of said frame, the step of placing the receptacle inside the opening being followed by a step of engaging said retaining element with said bottom. This prevents the receptacle from unintentionally lifting opposite the filling hole when the filling head is placed in cooperation with it.

Advantageously, this retaining element could be in the form of a bracket attached on the supporting frame once the receptacle is in place inside the opening, and positioned so that it is not obstructing the filling hole and the vent hole or holes.

In another advantageous arrangement, the closure member used comprises a closure frame having a recess, and an insert having the embossed and/or debossed surface and received in said recess.

Thus the insert, which the poured cosmetic product comes into contact with, can be designed as a solid insert made of a heat-resistant material having low adhesion to the poured cosmetic product, for example silicone, to facilitate unmolding when separating the receptacle and the closure member.

Alternatively, it is possible for the insert to be of some other solid material, such as a metal, and to have a step of applying a layer of a material having low adhesion to the poured cosmetic product, such as liquid silicone, to the surface or surfaces of the insert which the poured cosmetic product will touch, this application step preceding the step a) of positioning the receptacle on the closure member.

Similarly, if the closure member is made of a single piece, for example of metal, there can be a step of applying a layer of such a material having low adhesion to the poured cosmetic product onto the surface or surfaces, particularly the embossed and/or debossed surface, of the closure member which the poured cosmetic product will touch.

Besides, there may also be complementary positioning elements on the supporting frame and the closure frame, providing accurate and repeatable positioning of the receptacle held by the supporting frame relative to the embossed and/or debossed surface present on the closure member.

Advantageously, step b) of injecting the cosmetic product is preceded by a step in which the receptacle is preheated and at least the portion of the closure member having the embossed and/or debossed surface is preheated. This prevents the cosmetic product hot-poured into the receptacle from undergoing too much thermal shock when it comes in contact with the receptacle or the closure member, which could cause it to solidify instantly and prevent said cosmetic product from completely filling the filling cavity and/or completely penetrating the patterns defined on the embossed and/or debossed surface.

Preferably, step b) of injecting the cosmetic product is conducted while holding the receptacle, if applicable with the supporting frame, and the closure member at an angle relative to the horizontal direction so that the filling hole is placed vertically lower than the vent hole(s). In this manner, the hot-injected cosmetic product forces the air present in the filling cavity through the vent hole or holes, limiting the risk of air bubbles forming in the poured cosmetic product.

Another aim of the invention is to propose a method for manufacturing a cosmetic article having a decorative embossed and/or debossed surface formed of a plurality of different embossed and/or debossed surfaces, in particular by the pattern they define and/or by the color of the cosmetic products used to form them and/or by their respective heights relative to the bottom of the receptacle.

Thus in a particular embodiment of the method of the invention:
   the receptacle used has N filling areas, where N>1;
   N closure members are used, and
   N cycles comprising steps a) to c) are performed, the enclosed filling cavity of the nth cycle being defined in the nth filling area by: the receptacle, an nth closure member, and at least one of the cosmetic products poured in the previous cycles, for n>1.

In this embodiment, the receptacle comprises a plurality of filling areas extending from the bottom of the receptacle, each one having a filling hole and at least one associated vent hole, with these filling areas intended to be filled by cosmetic products of different colors and/or of different heights relative to the bottom of the receptacle and/or having different patterns on the surface.

During a first cycle, the cosmetic product is hot injected in a first filling area inside a first filling cavity defined by the receptacle and a first closure member. During the subsequent cycles, the cosmetic product is hot injected in each filling area inside a respective filling cavity defined by the receptacle, a corresponding closure member, and at least one of the cosmetic products poured in the previous cycles.

In this manner, no space is visible between the cosmetic products poured in the different filling areas once the cosmetic article is fully formed, the article presenting a continuous surface, with no gap at the interface between the cosmetic products poured in the different filling areas of the receptacle, as these adhere to each other at their areas of contact, and no gap at the walls of the receptacle. The method of this embodiment provides a cosmetic article presenting a completely clean transition, in color and/or texture, between the cosmetic products poured in the different receptacle filling areas, for the entire height of each poured cosmetic product, which substantially improves the aesthetics and the perceived production quality. This result is maintained throughout the shelf life and service life of the cosmetic article obtained.

Advantageously, one or more of the following arrangements may be used in this embodiment:
   for n between 1 and N−1, the nth closure member used also has at least one sealing portion that cooperates with the receptacle to prevent the cosmetic product from entering the filling areas intended to be filled during the following cycles;
   the method makes use of a closure frame having N recesses, each one accepting an insert having an embossed and/or debossed surface and, if applicable, the at least one sealing portion, the nth closure member used comprising said closure frame and the nth insert housed in the nth recess. Alternatively, the method may make use of a closure frame having a single recess adapted to receive N inserts in succession, each cycle n comprising the steps a) to c) being preceded by a step of extracting from said recess the insert used in the previous cycle, for n>1, and a step of placing the nth insert inside said recess;
   the embossed and/or debossed surfaces of the closure member used are protruding relative to the support surface for the supporting frame, to at least two different heights. Said different heights are at least equal to that of the rim of said supporting frame;
   between cycles n and n+1 comprising steps a) to c), a step is performed of cooling the cosmetic product poured during cycle n by exposure to room air and/or by means of a cooling plate and/or by means of a device that blows cold air;
   the cosmetic products poured in the different filling areas having different melting points, the N cycles comprising steps a) to c) are performed in the decreasing order of the melting point of the poured cosmetic products. This prevents the cosmetic product poured during cycle n from melting the cosmetic product or products poured during the previous cycles, which could affect the regularity and uniformity of the areas of contact between the cosmetic products;

the cosmetic products poured in the different receptacle filling areas have at least two different colors and/or two different textures and/or two different heights relative to the bottom of the receptacle;

the cosmetic products poured in the different receptacle filling areas have embossed and/or debossed surfaces adapted to define together a decorative embossed and/or debossed pattern on the visible side of the cosmetic article obtained. Such a decorative pattern could, for example, represent a logo, personalized text, a person or character, or a landscape, created from cosmetic products of different colors.

Advantageously, for any embodiment of the method of the invention, each filling area extends from a bottom portion which is associated with it and which has its filling hole and/or has its at least one vent hole in said associated bottom portion.

Preferably, each filling area has its filling hole and/or has its at least one vent hole in a peripheral section of the associated bottom portion.

Also preferably, for each filling area, the vent hole or holes are arranged as far as possible from each other, as well as from the filling hole, to allow the air to escape under the best possible conditions.

In addition, when a user has used up nearly all the cosmetic product or products contained inside the receptacle and has reached the bottom, it is unlikely that she will attempt to use the product remaining along the edge of the bottom portion associated with each filling area; thus the placement of the filling hole at an edge of the receptacle bottom portion associated with each filling area prevents this opening from being visible to the user who has used up nearly all the product found inside the receptacle filling area(s).

Other features and advantages of the invention will be apparent from reading the following description of one of its embodiments, provided as a non-limiting example, with reference to the attached drawings.

BRIEF DESCRIPTION OF THE DRAWINGS

In the drawings.

The same references are used to denote identical or similar elements in the various figures.

DETAILED DESCRIPTION OF THE DISCLOSURE

Figure 1:
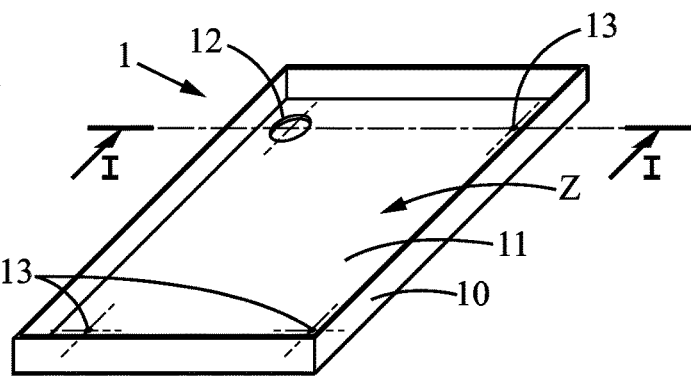
FIG. 1 is a perspective view of an empty receptacle having a single filling area, implemented in a first embodiment of the method of the invention.

In FIG. 1, a receptacle 1 as used in the manufacturing method of a first embodiment of the invention is represented. This receptacle has a cross-sectional shape that is rectangular or substantially rectangular, and comprises a bottom 11 and a peripheral wall 10 delimiting a filling area Z intended to accept a hot-poured cosmetic product CP such as lipstick, gloss, eyeliner, make-up foundation, or any other cosmetic product that can be hot poured.

In this first embodiment, the receptacle 1 used has a single filling area Z defined by the bottom 11 and the peripheral wall 10 of the receptacle 1, extending vertically from the bottom 11 of said receptacle 1 substantially to the edge of its peripheral wall. Associated with this filling area are a filling hole 12 and three vent holes 13 formed in the bottom 11 of the receptacle 1.

Advantageously, this filling hole 12, as well as the vent holes 13, are in a peripheral section of the bottom 11 of the receptacle, the vent holes 13 being diametrically opposite the filling hole 12 to be as distanced from it as possible. More specifically, the bottom 11 of the receptacle 1, and the single filling area Z associated with it, have a rectangular cross-sectional shape, with the filling hole 12 being placed at one angle of said bottom 11 and the vent holes being placed at three other angles of said bottom 11. Thus the hot-injected cosmetic product will be able to fill the cavity progressively while expelling the maximum volume of air and will do so in three principal directions associated with the rectangular shape of the bottom 11 of the receptacle 1.

The same principle of arranging the vent holes relative to the filling hole applies to all regular polygons.

Figure 2:
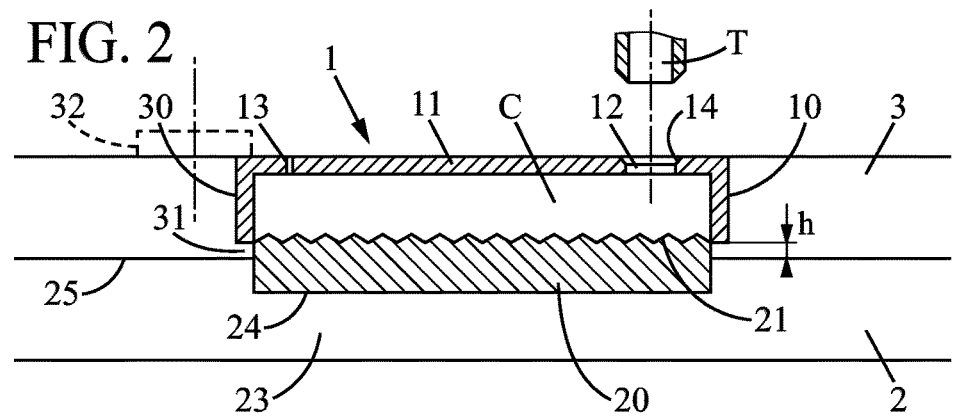
FIG. 2 is a cross-sectional view along line I-I, illustrating the receptacle held in a supporting frame positioned on the closure member according to the first embodiment of the method of the invention, before injection of the cosmetic product.

With reference to FIG. 2, the receptacle 1 cooperates with a closure member 2 to define an enclosed filling cavity C at the filling area Z. The cosmetic product CP which is hot injected through the filling hole 12 by a filling head T is intended to fill the cavity C so defined.

According to the invention, the cosmetic product CP poured into the receptacle is intended to have a decorative embossed and/or debossed surface S. The closure member 2 therefore has an embossed and/or debossed surface 21 that closes off the cavity C at the filling area Z of the receptacle 1. This surface 21 has an embossed and/or debossed pattern which gives the cosmetic product CP poured into the cavity C so defined a decorative surface S having a pattern complementary to that of the embossed and/or debossed surface 21.

As is can be seen in FIG. 2, the closure member 2 comprises a closure frame 23 which has a recess 24. An insert 20, having a top face which forms the embossed and/or debossed surface 21, is attached inside said recess by any appropriate means.

In a first step of the method of the first embodiment of the invention, the receptacle 1 is placed upside down on the closure member 2, so that the embossed and/or debossed surface 21 extends into the filling area Z. "Upside down" is understood to mean that the receptacle 1 is positioned on the closure member 2 so that the opening it delimits is oriented downwards, facing the embossed and/or debossed surface 21, thus defining with said surface 21 the enclosed filling cavity C.

Advantageously, and as can be seen in FIG. 2, the receptacle 1 may have been previously positioned upside down inside an opening 30 formed in a supporting frame 3 and equipped with a peripheral rim 31 on which the peripheral wall 10 of the receptacle 1 rests. The supporting frame 3 holding the receptacle 1 will then be placed on the closure member 2 so as to define the filling cavity C. As a variant, the supporting frame 3 may be positioned on the closure member 2 before the receptacle 1 is placed inside the opening 30 in the supporting frame 3.

Advantageously, the supporting frame 3 comprises at least one retaining element 32 that cooperates with the bottom 11 of the receptacle 1 to prevent said receptacle 1 from exiting the opening 30 once placed inside it. Illustrated as a dotted line in FIG. 2, the retaining element(s) may be in the form of one or more retaining tabs or one or more stop brackets 32, attached, for example by screwing them, to the supporting frame 3 once the receptacle 1 is in place inside the opening 30, and positioned to avoid obstructing the filling hole 12 and the vent hole(s) 13.

Besides, complementary positioning elements may be arranged on the closure member 2 and the supporting frame 3. These positioning elements ensure reliable and accurate positioning of the supporting frame 3, and therefore of the receptacle 1, on the closure member 2. These positioning elements may, for example, be positioning pins provided on one of the closure member 2 or the supporting frame 3 which cooperate with complementary openings formed in the other of the closure member 2 or the supporting frame 3.

Still with reference to FIG. 2, the closure frame 23 has a support surface 25 for the supporting frame 3. Once in place on the closure frame 23, the peripheral rim 31 of the supporting frame 3 rests on the support surface 25 of the closure frame 23.

As can be seen in FIG. 2, the embossed and/or debossed surface 21 of the insert 20 protrudes relative to the support surface 25 of the closure frame 23 and extends beyond it for a height corresponding to at least the height h of the rim 31 of the supporting frame 3. Thus a decorative embossed and/or debossed surface S can be formed on the cosmetic product CP poured into the cavity C, which does not extend vertically beyond the peripheral wall 10 of the receptacle 1, meaning it is at most flush with the peripheral wall 10 of the receptacle 1 on its open side.

Once the receptacle 1 is in place inside the supporting frame 3, with the retaining element(s) 32 cooperating with the bottom 11 of the receptacle 1, and the assembly formed by the supporting frame 3 and the receptacle 1 positioned on the closure member 2 so that the rim 31 of the supporting frame 3 rests on the support surface 25 of the closure frame 23 and the embossed and/or debossed surface 21 of the insert 20 extends into the filling area Z, a filling head T is brought into cooperation with the filling hole 12 in the bottom 11 of the receptacle 1 and a quantity of cosmetic product CP substantially corresponding to the volume of the cavity C is injected into said cavity C. During this injection step, the cosmetic product CP enters the cavity C, forces the air initially present in said cavity out the vent holes 13, and comes into contact with the embossed and/or debossed surface 21 of the insert 20.

A step of preheating the receptacle 1 and at least the insert 20 of the closure member 2 may be performed before the step of injecting the cosmetic product CP.

Advantageously, this injection step can be done while holding the assembly formed of the receptacle 1 placed inside the supporting frame 3 and the closure member 2 comprising the closure frame 23 and the insert 20, tilted relative to the horizontal direction so that the filling hole 12 is vertically lower than the vent holes 13. In this manner, the cosmetic product CP poured inside the cavity C forces the air initially present in the cavity out the vent holes 13, thus minimizing in an optimal manner the risk of air bubbles forming in the cosmetic product CP once it has cooled.

Next comes a step of cooling and at least partial solidification of the poured cosmetic product CP. This step may be done by placing the assembly formed by the receptacle 1 in the supporting frame 3 and the closure member 2 in room air or possibly by using a cooling plate or a device which blows cold air. After the cooling and at least partial solidification, the cosmetic product poured inside the cavity C adheres to the receptacle 1 in its filling area Z due to its contact with the peripheral wall 10 and the bottom 11, forming an integrally attached assembly with said receptacle 1.

If cosmetic product CP escaped through the vent holes 13 during the injection step, a step is performed of cleaning the back of the receptacle 1, meaning the side of the receptacle bottom 11 which is opposite the filling area Z, this step occurring either before or after the complete cooling or solidification of the poured cosmetic product CP.

After removing or disabling the retaining elements 32, the receptacle 1 containing the at least partially cooled and solidified cosmetic product CP is then extracted from the assembly formed by the supporting frame 3 and the closure member 2. This extraction of the receptacle 1 may, for example, be done by applying suction or magnetization to the outside surface of the bottom 11 of the receptacle 1. It is also possible to eject the receptacle 1 with an impact, by turning over the assembly formed by the supporting frame 3 holding the receptacle 1, and by the closure member 2, and tapping said assembly on a hard surface.

As a variant, the supporting frame 3 holding the receptacle 1 containing the cosmetic product CP can be separated from the closure member 2, then the receptacle 1 can be extracted from the supporting frame 3.

The cosmetic article A obtained, consisting of the receptacle 1 containing the cosmetic product CP, is then turned over so that it rests on the bottom 11 of the receptacle 1 and is placed in a storage area before its assembly into a final container, such as a makeup palette, as will be further described below.

Figure 3:
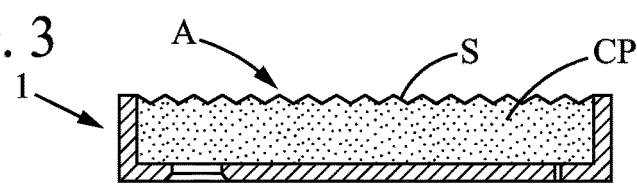
FIG. 3 is a cross-sectional view along line I-I, illustrating the receptacle after injection of the cosmetic product and separation of the closure member and the supporting frame, according to the first embodiment of the method of the invention.
Figure 4:
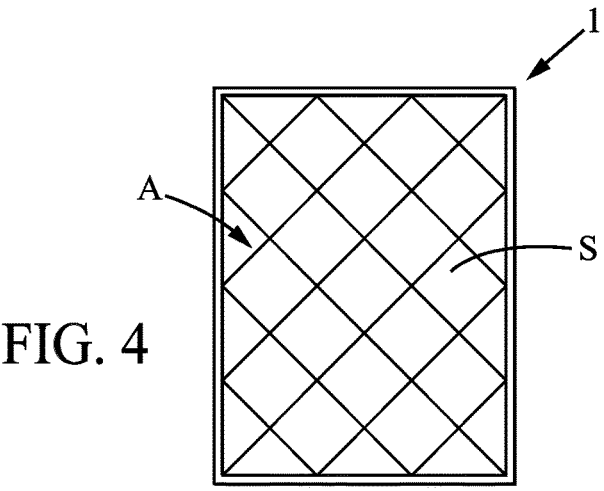
FIG. 4 is a top view of the cosmetic article having a decorative embossed and/or debossed surface obtained with the method of the first embodiment of the invention.

By using the method according to this first embodiment of the invention, a cosmetic article A is obtained which comprises a receptacle 1 containing a cosmetic product CP having a decorative embossed and/or debossed surface S extending to the edges of the receptacle 1, meaning fully touching its peripheral wall 10, and vertically extending so that it is at most flush with said peripheral wall 10, as can be seen in FIGS. 3 and 4 for example.

In a second embodiment of the method of the invention, a receptacle 1' is used comprising a plurality N of filling areas $Z_n$ extending from the bottom 11 of said receptacle 1', each one having a filling hole $12_n$ and at least one vent hole $13_n$, and as many closure members $2_n$ as there are filling areas $Z_n$.

Then N cycles are performed, comprising the following steps:

positioning the receptacle 1' on the nth closure member $2_n$, said member cooperating with the receptacle 1' to define an nth enclosed cavity $C_n$ at the nth filling area $Z_n$ and having an embossed and/or debossed surface $21_n$ adapted to give the nth cosmetic product $CP_n$ poured inside said nth cavity $C_n$ an nth decorative embossed and/or debossed surface $S_n$;

injecting the nth cosmetic product $CP_n$ into the nth filling cavity $C_n$ so defined, by means of a filling head $T_n$ inserted in an nth filling hole $12_n$ associated with the nth filling area $Z_n$; and separating the receptacle 1' containing the nth cosmetic product $CP_n$ in its nth filling zone $Z_n$ from the nth closure member $2_n$.

For the first cycle, meaning for n=1, the first filling cavity $C_1$ is defined in the first filling area $Z_1$ by the receptacle 1' and the first closure member $2_1$.

For the subsequent cycles, meaning for $1<n \leq 5$ N, the nth filling cavity $C_n$ is defined in the nth filling area $Z_n$ by the receptacle 1', the nth closure member $2_n$, and at least one of the cosmetic products $CP_i$, where i<n, poured in the previous cycles.

In this manner, at least one of the cosmetic products $CP_i$, where i<n, poured in the cycles prior to cycle n is used to define the nth filling cavity $C_n$.

Such an arrangement allows obtaining a cosmetic article A' having a decorative embossed and/or debossed surface formed by a plurality of cosmetic products $CP_n$ the mutual adjoining areas of which appear completely continuous, across their common heights. Thus, after all the filling areas $Z_n$ of the receptacle 1' have been filled, no space remains between the cosmetic products $CP_n$ which together with the receptacle 1' form the cosmetic article A' and which can be differentiated by their colors, their respective heights relative to the bottom 11 of the receptacle 1', and/or by the embossed and/or debossed pattern on their respective surfaces $S_n$.

This result is obtained directly after pouring the different cosmetic products and does not require a step of finishing the obtained cosmetic article to eliminate any gaps between the poured cosmetic products. The method of the invention is therefore particularly advantageous, especially in terms of manufacturing costs and the quality perceived by the user. In particular, because of these arrangements, the general appearance of the cosmetic article obtained can be maintained for its entire service life.

Preferably, a specific filling head $T_n$ is used for each poured cosmetic product $CP_n$.

In this second embodiment, starting with the first cycle and continuing to the next to last cycle, meaning for $1 \leq n < N$, the nth closure member $2_n$ is equipped with at least one sealing portion $22_n$ adapted to cooperate with the receptacle 1' to prevent the cosmetic product $SO_n$ poured during cycle n from entering the filling areas $Z_j$, j>n, intended to be filled during the subsequent cycles.

In a preferred form of this embodiment, the method makes use of a closure frame 23' having N recesses $24_n$ each receiving an insert $20_n$ having an embossed and/or debossed surface $21_n$ and, if applicable, the at least one sealing portion $22_n$. The nth closure member $2_n$ will then be formed of the closure frame 23' and the nth insert $20_n$ housed in the nth recess $24_n$.

Therefore in this embodiment, the receptacle 1' will be moved from cycle to cycle on the closure frame 23', so it successively cooperates with the different inserts 20, housed in their respective recess $24_n$.

Preferably, the receptacle 1' is received in a supporting frame 3 as described above, and said frame 3 supporting the receptacle 1' is moved from cycle to cycle on the closure frame 23'.

As a variant, the method may make use of a closure frame having a single recess adapted to receive N inserts $20_n$ in succession, each cycle n comprising steps a) to c) being preceded by a step of extracting from said recess the insert $20_{n-1}$ used in the previous cycle, for n>1, and a step of placing the nth insert $20_n$ inside said recess.

Advantageously, between cycles n and n+1, a step of cooling the cosmetic product $CP_n$ poured during cycle n is executed, by means of room air and/or a cooling plate and/or a device that blows cold air.

As a variant, in the manner described in relation to the first embodiment of the method of the invention, there may be a step of cooling the cosmetic product $CP_n$ poured during cycle n, between the steps of injecting cosmetic product $CP_n$ and separating the receptacle 1' from the closure member $2_n$ of each of the cycles n.

In the example illustrating this second embodiment and represented in FIGS. 5, 6a to 6c, 7 and 8, N is equal to three, meaning that the receptacle 1' used has three filling areas $Z_1$, $Z_2$ and $Z_3$, each extending from a bottom portion $11_1$, $11_2$, $11_3$ associated with it. Three closure members $2_1$, $2_2$, $2_3$ are therefore used and three cycles comprising the above steps are executed.

Figure 5:
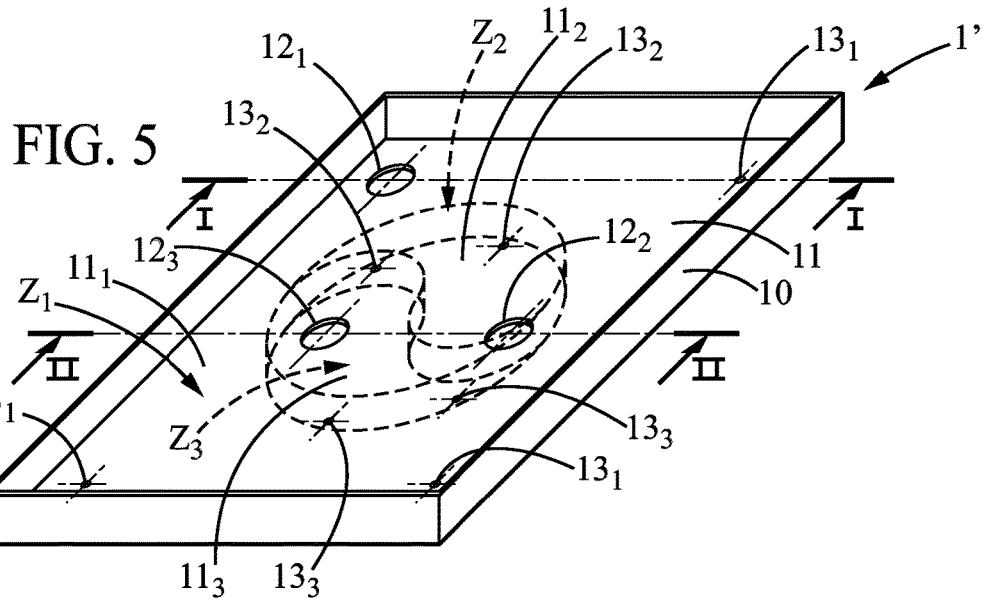
FIG. 5 is a perspective view of an empty receptacle having a plurality of filling areas, as used in a second embodiment of the method of the invention.

As can be seen in FIG. 5, in the example described, the receptacle 1' has three filling areas $Z_1$, $Z_2$ and $Z_3$ each having a respective filling hole $12_1$, $12_2$, $12_3$. The first filling area $Z_1$ has three vent holes $13_1$, and the second and third filling areas $Z_2$, $Z_3$ each have two vent holes denoted $13_2$ and $13_3$ respectively. Advantageously, these filling holes $12_1$, $12_2$, $12_3$ and vent holes $13_1$, $13_2$ and $13_3$ are placed in a peripheral section of the receptacle 1' bottom portion $11_1$, $11_2$, $11_3$ associated with each of the filling areas $Z_1$, $Z_2$ and $Z_3$.

Figure 6A:
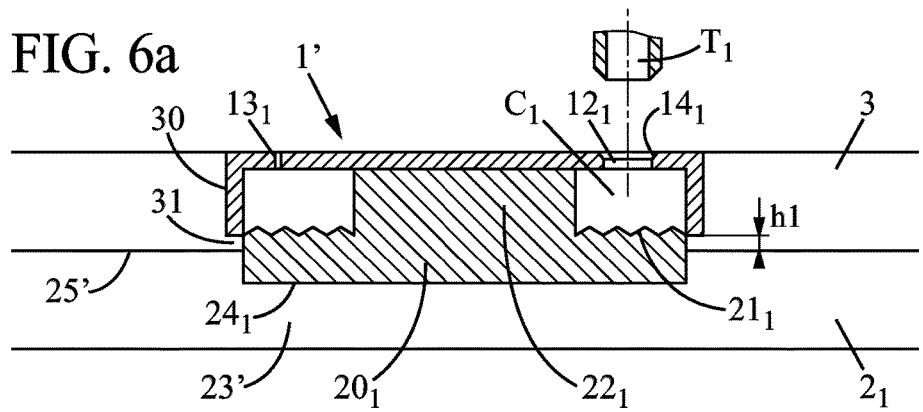
FIG. 6a is a cross-sectional view along line I-I, illustrating the receptacle held in a supporting frame positioned on a first closure member according to the second embodiment of the invention, before injection of a first cosmetic product in a first filling area.
Figure 6B:
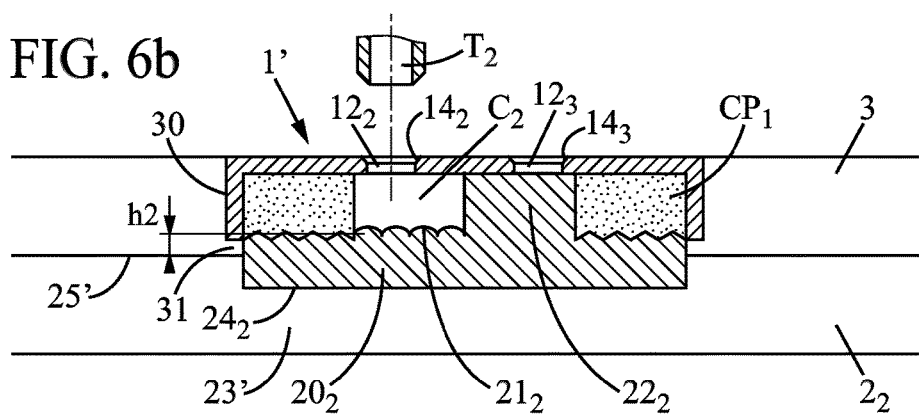
FIGS. 6b and 6c are cross-sectional views along line II-II, illustrating the receptacle held in the supporting frame respectively positioned on second and third closure member and illustrating the phases of injecting the cosmetic products in second and third filling areas, according to the second embodiment of the method of the invention.
Figure 6C:
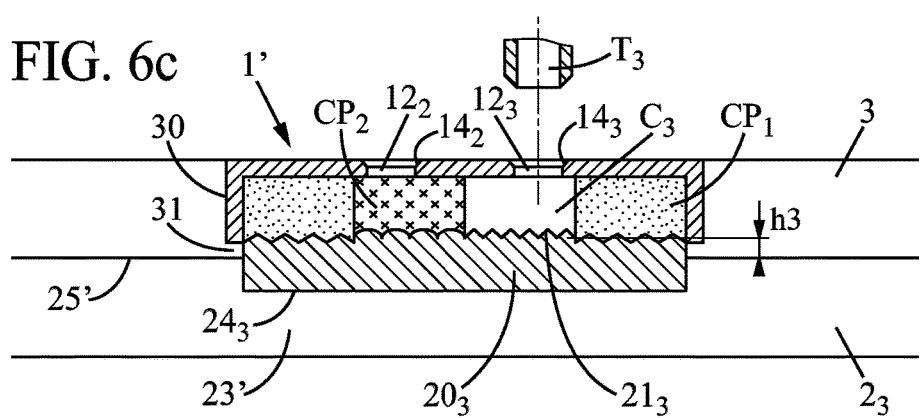

The three cycles executed to obtain the article A' according to this illustrative example of the second embodiment of the invention are now described, with reference to FIGS. 6a to 6c.

The method of this embodiment makes use of a frame 23' having three recesses $24_1$, $24_2$, $24_3$ inside of which corresponding inserts $20_1$, $20_2$, $20_3$ each having an embossed and/or debossed surface $21_1$, $21_2$, $21_3$ are intended to be fixed by any appropriate means.

Thus three closure members $2_1$, $2_2$, $2_3$ are used, each of these members comprising the frame 23' and an insert $20_1$, $20_2$, $20_3$ housed in a respective recess $24_1$, $24_2$, $24_3$ and having an embossed and/or debossed surface $21_1$, $21_2$, $21_3$.

As described in relation to the first embodiment, the receptacle 1' could, before being placed on the successive closure members $2_1$, $2_2$, $2_3$, be positioned upside down inside an opening 30 formed in a supporting frame 3 and equipped with a peripheral rim 31 on which the peripheral wall 10 of the receptacle 1' rests. The supporting frame 3 holding the receptacle 1' will then be put in place on the successive closure members $2_1$, $2_2$, $2_3$ so as to define the different filling cavities $C_1$, $C_2$, $C_3$, the peripheral rim 31 resting each time on a support surface 25' of the closure frame 23'.

As described above, this supporting frame 3 could be equipped with at least one retaining element that cooperates with the bottom 11 of the receptacle 1' to prevent said receptacle 1' from exiting the opening 30 once it is placed inside it.

Similarly, complementary positioning elements could advantageously be provided on the closure member $2_1$, $2_2$, $2_3$, in particular on the closure frame 23' common to the different closure member $2_1$, $2_2$, $2_3$, and on the supporting frame 3. Said positioning elements would ensure a reliable and accurate positioning of the supporting frame 3, and therefore of the receptacle 1', on the different closure members $2_1$, $2_2$, $2_3$.

When the method of the invention makes use of such a supporting frame 3, the embossed and/or debossed surface $21_1$, $21_2$, $21_3$ of each of the inserts $20_1$, $20_2$, $20_3$ may extend beyond the support surface 25' for the supporting frame 3 on the respective closure members $2_1$, $2_2$, $2_3$, here on the closure frame 23', by a same height corresponding to at least the height h of the rim 31. In this manner, one can form on the obtained cosmetic article A' a decorative embossed and/or debossed surface formed of a plurality of embossed and/or debossed surfaces $S_i$, $S_2$, $S_3$ not extending vertically beyond the peripheral wall 10 of the receptacle 1', meaning it is at most flush with said peripheral wall 10 of the receptacle 1' on its open side.

Alternatively, and as illustrated in FIGS. 6a to 6c and 7, the embossed and/or debossed surface $21_1$, $21_2$, $21_3$ of each of the inserts $20_1$, $20_2$, $20_3$ could extend to different heights h1, h2, h3 beyond the support surface 25' for the supporting frame 3 on the respective closure members $2_1$, $2_2$, $2_3$, each of these heights being at least equal to that of the rim 31. In this manner, one can form on the obtained cosmetic article A' a decorative embossed and/or debossed surface formed of several surfaces $S_1$, $S_2$, $S_3$ having different heights relative to the bottom 11 of the receptacle 1'.

The first of the three cycles executed to obtain the cosmetic article A according to this illustrative example of the second embodiment of the invention is now described with reference to FIG. 6a which represents a cross-sectional view along line I-I of FIG. 5.

As can be seen in this FIG. 6a, the receptacle 1', supported by the supporting frame 3, is placed upside down on the first closure member $2_1$. This first closure member $2_1$ has a first embossed and/or debossed surface $21_2$, as well as a first sealing portion $22_2$ defined by the first insert $20_1$. This first embossed and/or debossed surface $21_2$ protrudes relative to the support surface 25' of the closure frame 23' and extends beyond it by a height h1 substantially corresponding to the height h of the rim 31 of the supporting frame 3.

The first sealing portion $22_2$ protrudes relative to the support surface 25 of the closure frame 23 and cooperates with the bottom 11 of the receptacle 1' to occupy the volume defined by the receptacle 1' filling areas intended to be filled during the subsequent cycles, which are the second and third filling areas $Z_2$, $Z_3$ here. This prevents the cosmetic product $CP_1$ poured during the first cycle from entering the receptacle filling areas to be filled during the next cycles.

The first filling cavity $C_2$ which is to be filled during this first cycle is defined by the receptacle 1', particularly the bottom portion $11_1$ associated with the first filling area $Z_1$ and its peripheral wall 10, the first embossed and/or debossed surface $21_1$, and the first sealing portion $22_1$.

Once the assembly formed of the supporting frame 3 and the receptacle 1' is in place on the first closure member $2_1$, a first filling head $T_1$ is brought into cooperation with the first filling hole $12_1$ arranged in the bottom 11 of the receptacle 1', and a quantity of a first cosmetic product $CP_1$, substantially corresponding to the volume of said first cavity $C_1$ is injected into the first cavity $C_1$. During this injection step, the first cosmetic product $CP_1$ enters the cavity $C_1$, forces the air initially present in said cavity out the vent holes $13_1$, and comes into contact with the embossed and/or debossed surface $21_1$ as well as with the sealing portion $22_1$ of the first closure member $2_1$, and the peripheral wall 10 of the receptacle 1'.

Preferably, the first cosmetic product $CP_1$ poured inside the receptacle 1' is the one which has the highest melting point.

A step follows in which the first poured cosmetic product $CP_1$, is cooled and solidified. The first cosmetic product $CP_1$ poured into the first cavity $C_1$ then adheres to the receptacle 1' in its first filling area $Z_1$ due to its contact with the peripheral wall 10 and the bottom portion $11_1$ associated with it, forming an integrally attached assembly with said receptacle 1'.

The assembly formed of the supporting frame 3 and the receptacle 1' containing the cooled and solidified first cosmetic product $CP_1$ is then separated from the first closure member $2_1$ and the first cycle of the method according to the second embodiment of the invention is completed.

The assembly formed by the supporting frame 3 and the receptacle 1' is then placed upside down on the second closure member $2_2$, as can be seen in FIG. 6b which represents a cross-sectional view along line II-II of FIG. 5.

This second closure member $2_2$ has a second embossed and/or debossed surface $21_2$, as well as a second sealing portion $22_2$, both defined by the second insert $20_2$. This second embossed and/or debossed surface $21_2$ protrudes relative to the support surface 25' of the closure frame 23' and extends beyond it by a height h2 which is greater than the height h of the rim 31 of the supporting frame 3.

The second sealing portion $22_2$ protrudes relative to the support surface 25' of the closure frame 23' and cooperates with the bottom 11 of the receptacle 1' to occupy the volume defined by the receptacle 1 filling area intended to be filled during the next cycle, which is the third filling area $Z_3$ here.

In the example illustrated, the second insert $20_2$ also has a first embossed and/or debossed surface $21_1$, identical to the one present on the first insert $20_2$ and provided to cooperate with the cosmetic product $CP_1$ poured during the first cycle. In this manner, the embossed and/or debossed surface $S_1$ formed on the surface of the first poured cosmetic product $CP_1$ is protected during the pouring of the second cosmetic product $CP_2$.

Even so, it can be arranged so that this second insert $20_2$ has a smooth surface facing the first poured cosmetic product $CP_1$; in the embodiment illustrated, as the height h2 at which the embossed and/or debossed surface $21_2$ of the second insert $20_2$ is located relative to the support surface 25 is greater than the height h1 at which the embossed and/or debossed surface $21_2$ of the first insert $20_2$ is located, and therefore the height at which the embossed and/or debossed surface $S_1$ formed on the surface of the first cosmetic product poured $CP_1$ is located relative to the support surface 25', there is no risk of the cosmetic product $CP_2$ poured during the second cycle coming into contact and altering said embossed and/or debossed surface $S_1$ formed on the surface of the first cosmetic product poured $CP_1$.

The second filling cavity $C_2$ that is to be filled during this second cycle is defined by the receptacle 1', particularly the bottom portion $11_2$ associated with its second filling area $Z_2$, the second embossed and/or debossed surface $21_2$, the second sealing portion $22_2$, and the cosmetic product $CP_1$ poured during the first cycle and completely solidified.

Once the assembly formed of the supporting frame 3 and the receptacle 1' is in place on the second closure member $2_2$, a second filling head $T_2$ is brought into cooperation with the second filling hole $12_2$ arranged in the bottom 11 of the receptacle 1' and an amount of second cosmetic product $CP_2$ substantially corresponding to the volume of said second cavity $C_2$ is injected into the second cavity $C_2$. During this injection step, the second cosmetic product $CP_2$ enters the second cavity $C_2$, forces the air initially present in said cavity out through the vent holes $13_2$, and comes in contact with the embossed and/or debossed surface $21_2$ and the sealing portion $22_2$ of the second closure member $2_2$, as well as with the cosmetic product $CP_1$ poured during the first cycle, adhering to it at the interface where they touch.

Preferably, the second cosmetic product $CP_2$ poured into the receptacle 1' has a lower melting point than the one of the first cosmetic product $CP_1$. This prevents the second cosmetic product $CP_2$ poured into the receptacle 1' from causing the first cosmetic product $CP_1$ present inside the receptacle 1' to melt.

Next comes a new step of cooling and solidification of the second cosmetic product poured $CP_2$. The second cosmetic product $CP_2$ poured into the second cavity $C_2$ then adheres to the receptacle 1' in its second filling area $Z_2$ due to its contact with the bottom portion $11_2$ associated with it, as well as with the cosmetic product $CP_1$ poured during the first cycle, forming an integrally attached assembly with said receptacle 1' and said cosmetic product $CP_1$ poured during the first cycle.

The assembly formed of the supporting frame 3 and the receptacle 1' containing the first and second cooled and solidified cosmetic products $CP_1$, $CP_2$ is then separated from the second closure member $2_2$, and the second cycle of the method according to the second embodiment of the invention is completed.

The assembly formed of the supporting frame 3 and the receptacle 1' is then placed upside down on the third closure member $2_3$, as can be seen in FIG. 6c which represents a cross-sectional view along line II-II of FIG. 5.

This third closure member $2_3$ has a third embossed and/or debossed surface $21_3$, but unlike the first two closure members $2_1$ and $2_2$ it has no sealing portion. This third embossed and/or debossed surface $21_3$ protrudes relative to the support surface 25' of the closure frame 23' and extends beyond it by a height h3 that is greater than the height h of the rim 31 of the supporting frame 3, and is substantially equal to the height h2 at which the embossed and/or debossed surface $21_2$ of the second insert $20_2$ is located relative to the support surface 25'.

In the illustrated embodiment, the third insert $20_3$ also has first and second embossed and/or debossed surfaces $21_1$, $21_2$ identical to those present on the first and second inserts $20_1$, $20_2$ and provided to cooperate with the cosmetic products $CP_1$, $CP_2$ poured during the first and second cycles. In this manner, the embossed and/or debossed surfaces $S_1$, $S_2$ formed on the surfaces of the first and second cosmetic products poured $CP_1$, $CP_2$ are protected when the third cosmetic product $CP_3$ is poured.

The third filling cavity $C_3$ that is to be filled during this third cycle is defined by the receptacle 1', particularly the bottom portion $11_3$ associated with its third filling area $Z_3$, the third embossed and/or debossed surface $21_3$, and the cosmetic products $CP_1$ and $CP_2$ poured during the first and second cycles and completely solidified.

Once the assembly formed of the supporting frame 3 and the receptacle 1' is in place on the third closure member $2_3$, a third filling head $T_3$ is brought into cooperation with the third filling hole $12_3$ arranged in the bottom 11 of the receptacle 1', and a quantity of a third cosmetic product $CP_3$ substantially corresponding to the volume of said third cavity $C_3$ is injected into said third cavity $C_3$. During this injection step, the third cosmetic product $CP_3$ enters the cavity $C_3$, forces the air initially present in said cavity out through the vent holes $13_3$, and comes in contact with the embossed and/or debossed surface $21_3$ of the third closure member $2_2$ as well as with the cosmetic products $CP_1$ and $CP_2$ poured during the first and second cycles, adhering to them at their respective interfaces where they touch.

Preferably, the third cosmetic product $CP_3$ poured into the receptacle 1' has a lower melting point than the ones of the first and second cosmetic products $CP_1$, $CP_2$. This prevents the third cosmetic product $CP_3$ poured into the receptacle 1' from causing the first and second cosmetic products $CP_1$, $CP_2$ present in the receptacle 1' to melt.

A new step follows, in which the third cosmetic product poured $CP_3$ is cooled and solidified. The third cosmetic product $CP_3$ poured into the third cavity $C_3$ then adheres to the receptacle 1' in its third filling area $Z_3$ due to its contact with the associated bottom portion $11_3$, as well as with the cosmetic products $CP_1$ and $CP_2$ poured during the first and second cycles, forming an integrally attached assembly with said receptacle 1' and with said cosmetic products $CP_1$ and $CP_2$.

The assembly formed of the supporting frame 3 and the receptacle 1' containing the first, second, and third cooled and solidified cosmetic products $CP_1$, $CP_2$, $CP_3$ is then separated from the third closure member $2_3$, and the third cycle of the method according to the second embodiment of the invention is completed.

The integrally attached assembly comprising the receptacle 1' and the cooled and solidified cosmetic products $CP_1$, $CP_2$, $CP_3$, having a decorative embossed and/or debossed surface consisting of the different embossed and/or debossed surfaces $S_1$, $S_2$, $S_3$, is then ejected from the supporting frame 3 and turned back over to rest on its bottom 11 for storage in a storage area before its assembly into a final container such as a makeup palette, as will be described below.

Figure 8:
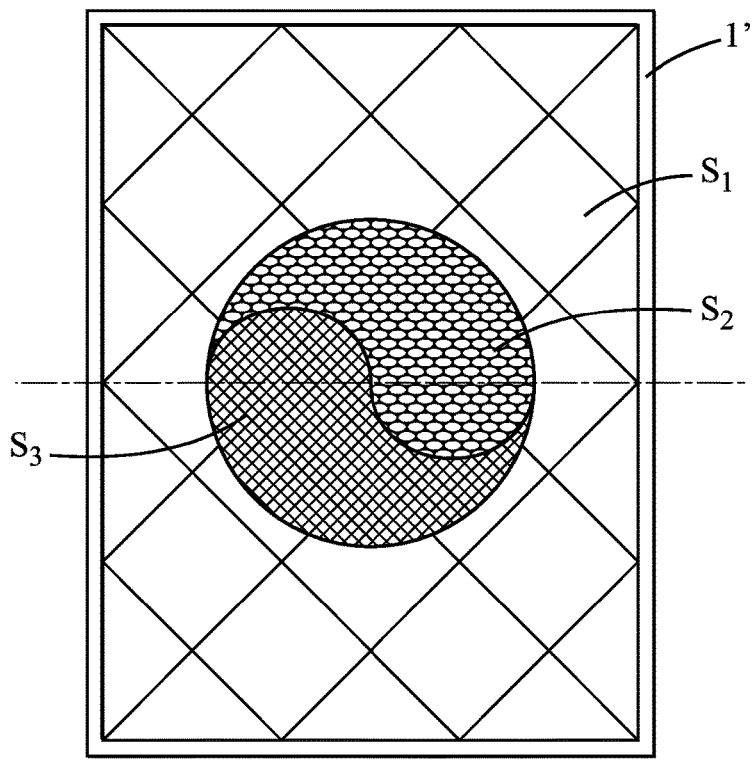
FIG. 8 is a top view of the cosmetic article, having a decorative embossed and/or debossed surface obtained with the method of the second embodiment of the invention.
Figure 7:
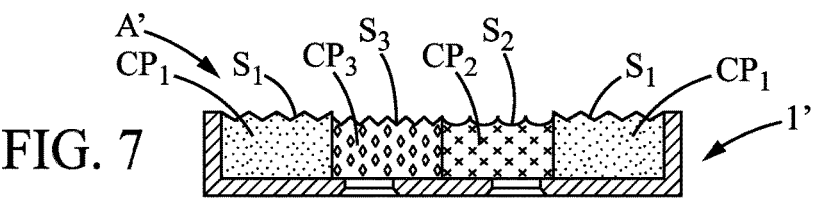
FIG. 7 is a cross-sectional view along line II-II, illustrating the receptacle after injection of the cosmetic products and separation of the last closure member and the supporting frame, according to the second embodiment of the method of the invention.

Using the method of this second embodiment of the invention, a cosmetic article A' is obtained which comprises a receptacle 1' containing cosmetic products $CP_1$, $CP_2$, $CP_3$ having a decorative embossed and/or debossed surface consisting of different embossed and/or debossed surfaces $S_1$, $S_2$, $S_3$, extending out to the edges of the receptacle 1', meaning they fully touch its peripheral wall 10, extending in the vertical direction to be substantially flush with said peripheral wall 10, as can be seen for example in FIGS. 7 and 8.

The cosmetic products $CP_1$, $CP_2$, $CP_3$ poured according to the method of this second embodiment differ in their color, texture, and/or composition. Using this method it is therefore possible to form a cosmetic article having a decorative embossed and/or debossed surface having different areas consisting of cosmetic products $CP_1$, $CP_2$, $CP_3$, these areas being intertwined and/or nested inside one another and/or having different heights h1, h2, h3 where h1>h2, and h2 and h3 are substantially equal.

In the embodiment illustrated, the assembly consisting of the three poured cosmetic products $CP_1$, $CP_2$, $CP_3$ defines a central decorative embossed and/or debossed pattern (debossed here) on the side exposed to the user of the obtained cosmetic article. This pattern is in the form of the well-known yin and yang symbol, as can be seen in FIG. 8.

In either of the embodiments of the method of the invention, the inserts 20, $20_n$ used may advantageously be made of solid silicone or any other material that will limit the adhesion of the poured cosmetic products CP, $CP_n$ to the surfaces of the inserts 20, $20_n$ they will be in contact with, particularly the embossed and/or debossed surfaces 21, $21_n$, and facilitate unmolding the cosmetic products CP, $CP_n$ after cooling without damaging the decorative embossed and/or debossed surfaces S, $S_n$.

Alternatively, the inserts 20, $20_n$ may be made of metal; in this case, there may be an advantageous preliminary step of applying a layer of liquid silicone or another liquid substance with low adhesion to the poured cosmetic products CP, $CP_n$, for example by spraying or dabbing, on the surfaces of the inserts 20, $20_n$ they will be in contact with, particularly the embossed and/or debossed surfaces 21, $21_n$, before the receptacle 1 is positioned on the closure members 2, $2_n$.

For any embodiment of the method of the invention, the filling hole(s) 12, $12_n$ may have a circular or substantially circular cross-sectional shape, of reduced diameter, for example between 1 and 5 mm, and preferably of about 2 mm. The vent holes 13 may have any cross-sectional shape, for example a circle, square, oval, etc., with the largest dimension being substantially on the order of a tenth of a millimeter, and preferably near 0.3 mm.

The filling hole(s) 12, $12_n$ are advantageously beveled 14, $14_n$ where they exit the receptacle 1, 1', meaning on the outside face of the bottom 11. These bevels 14, $14_n$, cooperate with filling heads T, $T_n$ having injection ends of a complementary shape in order to define a fluid-tight contact between said heads T, $T_n$, and said holes 12, $12_n$. To ensure or further improve this fluid-tight seal between the different filling heads T, $T_n$ and the filling holes 12, $12_n$, the filling head T, $T_n$ may also be fitted with a sheath made of a sealing material, such as a silicone sheath.

For physicochemical compatibility with the various cosmetic products poured CP, $CP_n$, the receptacle 1, 1' used in the manufacturing method according to either of the described embodiments will preferably be made of a material which has no risk of interaction with these cosmetic products, such as aluminum.

The receptacle 1, 1' containing the cosmetic product(s) CP, $CP_n$, once they are completely cooled and solidified, is intended to be affixed to a final container for cosmetic articles, such as a makeup palette. It may be affixed by gluing, for example placing glue or an adhesive sticker between the bottom of the receptacle and the makeup palette, or by magnetization. In the latter case, if the receptacle used is made of aluminum, an intermediate metal receptacle is provided which is adapted to receive the receptacle containing the cosmetic product(s) and to be attached magnetically to the palette. A device adapted to retain the receptacle containing the cosmetic product(s) inside the intermediate receptacle will then be provided to ensure that these two elements are integrally attached. This retaining device could, for example, be in the form of a snap-on device such as an inner peripheral ridge on the seating for the receptacle, intended to cooperate with a complementary indentation formed in the peripheral wall of the receptacle 1 containing the cosmetic product(s).

Lastly, although the examples described represent a receptacle having a cross-sectional shape that is generally rectangular, a receptacle of the method of the invention can be used that has a cross-sectional shape that is circular, oval, polygonal, or any other desired shape.

The invention claimed is:

1. A method for manufacturing a cosmetic article having a decorative embossed and/or debossed surface, based on at least one cosmetic product hot-poured into a container, wherein said method makes use of:
   a receptacle forming said container and having a peripheral wall and a bottom, said receptacle having at least one filling area, each filling area extending from the bottom of said receptacle and having a filling hole and at least one vent hole,
   a closure member that cooperates with the receptacle to define an enclosed filling cavity with the at least one filling area, and having an embossed and/or debossed surface adapted to give the cosmetic product poured into said cavity an embossed and/or debossed surface, said method comprising at least the following steps:
   a) positioning the receptacle on the closure member so that the embossed and/or debossed surface extends into the filling area;
   b) hot injecting the cosmetic product into the filling cavity by means of a filling head inserted in the filling hole;
   c) separating the receptacle from the closure member, making use of a supporting frame having an opening for receiving the receptacle, said opening having a peripheral rim of a certain height, wherein the closure member has a support surface for the supporting frame, the embossed and/or debossed surface protruding beyond said support surface to a height that is at least equal to that of said rim, said method additionally comprising:
   a step consisting of placing the receptacle inside the opening of the supporting frame so that the peripheral wall of said receptacle rests on the rim; a step consisting of positioning the supporting frame equipped with the receptacle on the closure member so that said rim rests on the support surface of said closure member; and a step consisting of separating the receptacle from the supporting frame.

2. The method according to claim 1, wherein the closure member used comprises a closure frame having a recess, and an insert having an embossed and/or debossed surface and received in said recess.

3. The method according to claim 1, wherein step b) is carried out while holding the receptacle with the supporting frame, and the closure member at an angle relative to the horizontal direction so that the filling hole is placed vertically lower than the vent hole(s).

4. The method according to claim 1, wherein: the receptacle used has N filling areas, where N>1; N closure members are used, and N cycles comprising steps a) to c) are performed, the enclosed filling cavity of the nth cycle being defined in the nth filling area by: the receptacle, an nth closure member, and at least one of the cosmetic products poured in the previous cycles, for n>1.

5. The method according to claim 4, wherein, for n between 1 and N−1, the nth closure member used also has at least one sealing portion that cooperates with the receptacle to prevent the cosmetic product from entering the filling areas intended to be filled during the following cycles.

6. The method according to claim 4, making use of a closure frame having N recesses, each one accepting an insert having an embossed and/or debossed surface and, if applicable, the at least one sealing portion, the nth closure member used comprising said closure frame and the nth insert housed in the nth recess.

7. The method according to claim 4, wherein the embossed and/or debossed surfaces of the closure members used are protruding relative to the support surface for the supporting frame, to at least two different heights that are at least equal to that of the rim.

8. The method according to claim 4, wherein the cosmetic products poured in the different filling areas of the receptacle have at least two different colors and/or two different textures and/or two different heights relative to the bottom of the receptacle.

9. The method according to claim 4, wherein the cosmetic products poured in the different filling areas of the receptacle have embossed and/or debossed surfaces adapted to define together a decorative embossed and/or debossed pattern on the visible side of the cosmetic article obtained.

10. The method according to claim 1, wherein each filling area extends from a bottom portion which is associated with it and which has its filling hole and/or has its at least one vent hole in said associated bottom portion.

11. The method according to claim 10, wherein each filling area has its filling hole and/or has its at least one vent hole in a peripheral section of the associated bottom portion.

12. The method according to claim 11, wherein said at least one vent hole is arranged a far as possible from said filling hole for each filling area.

13. A method for manufacturing a cosmetic article having a decorative embossed and/or debossed surface, based on at least one cosmetic product hot-poured into a container, wherein said method makes use of: a receptacle forming said container and having a peripheral wall and a bottom, said receptacle having at least one filling area, each filling area extending from the bottom of said receptacle and having a filling hole and at least one vent hole, a closure member that cooperates with the receptacle to define an enclosed filling cavity with the at least one filling area, and having an embossed and/or debossed surface adapted to give the cosmetic product poured into said cavity an embossed and/or debossed surface, said method comprising at least the following steps:
 a) positioning the receptacle on the closure member so that the embossed and/or debossed surface extends into the filling area;
 b) hot injecting the cosmetic product into the filling cavity by means of a filling head inserted in the filling hole;
 c) separating the receptacle from the closure member, wherein:
 the receptacle used has N filling areas, where N>1;
 N closure members are used, and
 N cycles comprising steps a) to c) are performed, the enclosed filling cavity of the nth cycle being defined in the nth filling area by: the receptacle, an nth closure member, and at least one of the cosmetic products poured in the previous cycles, for n>1.

14. The method according to claim 13, wherein, for n between 1 and N−1, the nth closure member used also has at least one sealing portion that cooperates with the receptacle to prevent the cosmetic product from entering the filling areas intended to be filled during the following cycles.

15. The method according to claim 13, making use of a closure frame having N recesses, each one accepting an insert having an embossed and/or debossed surface and, if applicable, the at least one sealing portion, the nth closure member used comprising said closure frame and the nth insert housed in the nth recess.

16. The method according to claim 13, wherein the embossed and/or debossed surfaces of the closure members used are protruding relative to the support surface for the supporting frame, to at least two different heights that are at least equal to that of the rim.

17. The method according to claim 13, wherein the cosmetic products poured in the different filling areas of the receptacle have at least two different colors and/or two different textures and/or two different heights relative to the bottom of the receptacle.

18. The method according to claim 13, wherein the cosmetic products poured in the different filling areas of the receptacle have embossed and/or debossed surfaces adapted to define together a decorative embossed and/or debossed pattern on the visible side of the cosmetic article obtained.

* * * * *